US010765480B2

United States Patent
Srimohanarajah et al.

(10) Patent No.: US 10,765,480 B2
(45) Date of Patent: Sep. 8, 2020

(54) WIRELESS ACTIVE TRACKING FIDUCIALS

(71) Applicants: SYNAPTIVE MEDICAL (BARBADOS) INC., Bridgetown (BB); Kirusha Srimohanarajah, Toronto (CA); Gal Sela, Toronto (CA); Kelly Noel Dyer, Toronto (CA)

(72) Inventors: Kirusha Srimohanarajah, Toronto (CA); Gal Sela, Toronto (CA); Kelly Noel Dyer, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 474 days.

(21) Appl. No.: 15/543,803

(22) PCT Filed: Aug. 17, 2016

(86) PCT No.: PCT/CA2016/050963
§ 371 (c)(1),
(2) Date: Jul. 14, 2017

(87) PCT Pub. No.: WO2018/032084
PCT Pub. Date: Feb. 22, 2018

(65) Prior Publication Data
US 2018/0325621 A1 Nov. 15, 2018

(51) Int. Cl.
A61B 34/00 (2016.01)
A61B 34/20 (2016.01)
A61B 90/00 (2016.01)
A61B 17/00 (2006.01)

(52) U.S. Cl.
CPC ............. A61B 34/00 (2016.02); A61B 34/20 (2016.02); A61B 2017/00115 (2013.01); A61B 2017/00154 (2013.01); A61B 2017/00734 (2013.01); A61B 2034/2055 (2016.02); A61B 2034/2068

(Continued)

(58) Field of Classification Search
CPC . A61B 34/00; A61B 34/20; A61B 2034/2057; A61B 2034/2068;
(Continued)

(56) References Cited

U.S. PATENT DOCUMENTS 5,920,395 A 7/1999 Schulz
6,608,688 B1 * 8/2003 Faul ............... G06F 3/0325
356/614

(Continued)

FOREIGN PATENT DOCUMENTS

KR 101010289 B1 * 1/2011 ......... A61B 17/1227

OTHER PUBLICATIONS

Machine translation of Shin et al. (KIPO Pub. No. KR 101010289 B1, Jan. 27, 2011).*

(Continued)

Primary Examiner — Carolyn A Pehlke
(74) Attorney, Agent, or Firm — Rowand LLP

(57) ABSTRACT

A fiducial marker to be tracked by a surgical navigation system. The fiducial marker is to be affixed to an object during a surgical procedure. The fiducial marker including a casing for attachment to the object; a light emitting component attached to the casing; a power source within the casing; a signal receiver to receive a signal from the surgical navigation system; and control logic to control the light emitting component in response to the signal from the surgical navigation system. The object to-be-tracked may include a plurality of the fiducial markers arranged in geometric pattern, and the markers may include a first active fiducial marker having a first light emitting component that emits light having a first spectral bandwidth, and a second active fiducial marker having a second light emitting component that emits light having a second spectral bandwidth different from the first spectral bandwidth.

21 Claims, 7 Drawing Sheets

(52) U.S. Cl.
CPC ......... (2016.02); *A61B 2090/3945* (2016.02); *A61B 2090/3979* (2016.02)

(58) Field of Classification Search
CPC .... A61B 2034/2072; A61B 2034/2074; A61B 2034/2055; A61B 2034/2046; A61B 2090/3975; A61B 2090/3979; A61B 2090/3983; A61B 2090/3945; A61B 2017/00115; A61B 2017/00154; A61B 2017/00734; G02B 6/0021; G02B 6/0073
See application file for complete search history.

(56) References Cited

U.S. PATENT DOCUMENTS

| | | | |
|---|---|---|---|
| 6,675,040 B1 * | 1/2004 | Cosman | G06T 3/00 600/427 |
| 7,850,362 B2 * | 12/2010 | Yu | F21V 19/0005 362/647 |
| 8,412,308 B2 | 4/2013 | Goldbach | |
| 2001/0034530 A1 * | 10/2001 | Malackowski | A61B 90/36 606/130 |
| 2003/0095186 A1 | 5/2003 | Aman et al. | |
| 2008/0021311 A1 | 1/2008 | Goldbach | |
| 2008/0161682 A1 | 7/2008 | Kendrick et al. | |
| 2008/0200794 A1 * | 8/2008 | Teichman | A61B 90/39 600/407 |
| 2011/0184690 A1 | 7/2011 | Iida et al. | |

OTHER PUBLICATIONS

WIPO, International Search Report and Written Opinion relating to PCT application No. PCT/CA2016/050963, dated May 18, 2017.

* cited by examiner

WIRELESS ACTIVE TRACKING FIDUCIALS

FIELD

The present application generally relates to image-guided medical procedures. More particularly, the subject matter of the present disclosure relates to the field of patient reference tools for rapid registration in relation to image-guided medical procedures.

BACKGROUND

Surgical navigation systems may rely upon optical tracking of objects in the operating room using cameras. The system attempts to detect fiducial markers attached to the object in the images captured by the cameras and then determine the three-dimensional location and orientation of the object. In many cases, the fiducial markers are passive reflective spheres arranged in a fixed geometrical pattern.

BRIEF SUMMARY

In one aspect, the present application describes a fiducial marker to be tracked by a surgical navigation system, the fiducial marker to he affixed to an object during a surgical procedure, the surgical navigation system to estimate the location of the object during the surgical procedure based on determining the location of the fiducial marker. The fiducial marker includes a casing for attachment to the object; a light emitting component attached to the casing; a power source within the casing; a signal receiver to receive a signal from the surgical navigation system; and control logic to control the light emitting component in response to the signal from the surgical navigation system.

In another aspect, the present application discloses an optical navigation system for active tracking of objects for use in a medical procedure. The system includes a plurality of independent active fiducial markers attached to a rigid body, including a first active fiducial marker having a first light emitting component that emits light having a first spectral bandwidth, and a second active fiducial marker having a second light emitting component that emits light having a second spectral bandwidth different from the first spectral bandwidth; each of the active fiducial markers having its own internal power source for powering its respective light emitting component; and at least one optical tracking camera to detect and distinguish between light from the first active fiducial marker and light from the second active fiducial marker based upon a difference in the first and second spectral bandwidths.

In a further aspect, the present application describes an optical navigation system for active tracking of objects for use in a medical procedure. The system includes a plurality of independent active fiducial markers attached to a rigid body, including a first active fiducial marker having a first light emitting component that emits light having a first pulse pattern, and a second active fiducial marker having a second light emitting component that emits light having a second pulse pattern different from the first pulse pattern; each of the active fiducial markers having its own internal power source for powering its respective light emitting component; and at least one optical tracking camera to detect and distinguish between light from the first active fiducial marker and light from the second active fiducial marker based upon the difference in the first and second pulse patterns.

In yet another aspect, the present application describes a system for use in active tracking of objects for use in a medical procedure. The system includes a fiducial frame to be attached to a trackable object, the fiducial frame having a plurality of support posts positioned in a geometric pattern; a power source attached to the fiducial frame; a master control and sync unit attached to the fiducial frame and coupled to the power source; a plurality of fiducial markers, each fiducial marker including a light emitter and a casing for attachment to a respective one of the support posts; and signal lines, each signal line connecting one of the fiducial markers to the master control and sync unit.

In yet a further aspect, the present application describes non-transitory, computer-readable media storing computer-executable program instructions which, when executed, configured a processor to perform the described methods.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of or . . . " is intended to cover any one or more of the listed elements, including any one of the listed elements alone, any sub-combination, or all of the elements, without necessarily excluding any additional elements, and without necessarily requiring all of the elements.

BRIEF DESCRIPTION OF THE DRAWINGS

Reference will now be made, by way of example, to the accompanying drawings which show example embodiments of the present application.

Similar reference numerals may have been used in different figures to denote similar components.

DESCRIPTION OF EXAMPLE EMBODIMENTS

Figure 1:
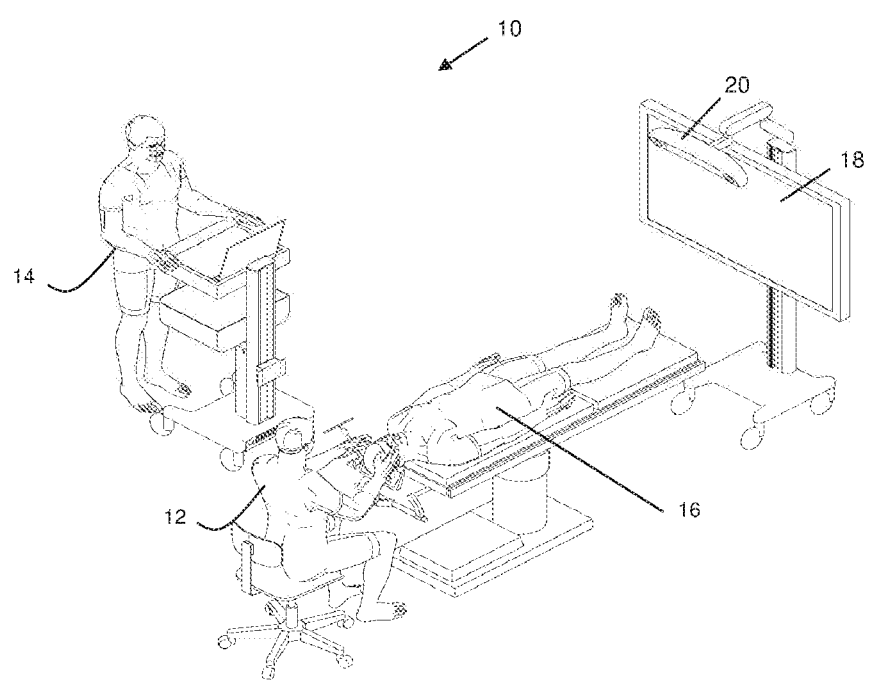
FIG. 1 shows a perspective view of an example surgical navigation system in an operating room environment.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera. These optical tracking systems also require a reference to the patient to know where the instrument is relative to the target (e.g., a tumour) of the medical procedure. Image-guided surgical procedures typically involve using a surgical instrument, such as a fibre optic scope, an optical coherence tomography (OCT) probe, a micro ultrasound transducer, an electronic sensor or stimulator, or an access port based tool.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principles available with each modality. CT is often used to visualize bony structures and blood vessels when used in conjunction with an intra-venous agent such as an iodinated contrast agent. MRI may also be performed using a similar contrast agent, such as an intra-venous gadolinium-based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

During a medical procedure, navigation systems require a registration to transform between the physical position of the patient in the operating room and the volumetric image set (e. MRI/CT) being navigated to. Conventionally, this registration is done to the position of a reference tool, which is visible by the tracking system and stays fixed in position and orientation relative to the patient throughout the procedure.

Pre-operative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the pre-operative scans, allowing for instruments to be viewed on a monitor in the context of the pre-operative information.

This registration is typically accomplished through correspondence touch points (e.g., either fiducial or anatomic points). Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position. Another conventional approach to collecting the touch points includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the conventional approaches to registration discussed above include a stylus that needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration lost, re-registration is difficult to be completed again during the surgical procedure.

As noted above, one technique for tracking an object using an optical navigation system is to place reflective fiducial markers on the object. In some cases, the fiducial markers are infrared light reflective and the navigation system includes an infrared light source to illuminate the fiducial markers.

FIG. 1 illustrates, in a perspective view, a navigation system 10, such as a surgical navigation system, in an environmental context, such as an operation room (OR). The navigation system 10 supports, facilitates, and enhances a surgical procedure. By example only, a surgeon 12 conducts a minimally-invasive access port based surgery on a subject, such as a patient 16, in an OR environment. The navigation system 10 may include a navigation camera 20, which may include at least two cameras spaced-apart to capture stereoscopic images. The navigation system 10 may be used track at least one instrument, such as a surgical instrument, for assisting the surgeon 12 during the surgical procedure. By example only, an operator 14 is also present to operate, control, and provide assistance for the system 10, The navigation system 10 may further include one or more display screens 18 on which the navigation system 10 may display, for example, a patient rendering overlaid with pre-operative imaging data and together with a rendering of the object(s) being tracked relative to the patient. In this manner the surgeon 12 is able to observe the location of the object(s), like an access port or probe, relative to structure and features identifiable in the pre-operative imaging data. This may permit the surgeon 12 to target and/or avoid specific areas that are not readily visible to the surgeon 12 while performing the surgery.

In some cases, to track an object, a plurality of passive fiducial markers are attached to the object by mounting them to a rigid body attached to the object. The rigid body (e.g. a frame) to which the passive fiducial markers are attached positions them in a defined geometric pattern so that the optical navigation system is able to determine the three-dimensional position of the frame and, thus, the position of the object to which it is attached.

Figure 2:
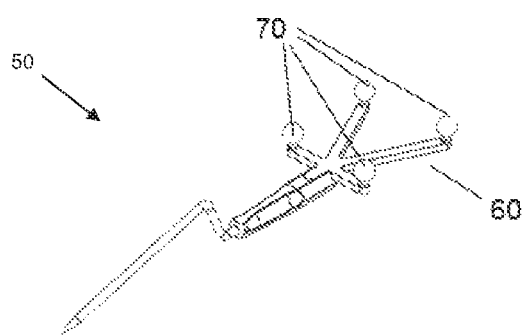
FIG. 2 shows an example of a tracked object.

FIG. 2 shows, in a perspective view, an example of a tracked object. In this example, the object is a pointer 50, in accordance with an embodiment of the present disclosure. The pointer 50 includes a plurality of fiducial markers 70 disposed on a frame 60 attached to the pointer 50. In this case, the example shows four fiducial markers 70, although a minimum of three tracking markers 70 would typically be required by the navigation system to determine the location of the tip of the pointer 50 and its axis in three-dimensional space.

Some tracking systems may use active fiducial markers. For example, there are virtual reality or augmented reality systems where the tracking marker is a stationary power or wired location with a pattern of active fiducial markers emitting light. The camera or cameras are mounted to a mobile item, like a YR headset. In that case, the marker serves as a stationary reference point within the three-dimensional space and the camera is on the device being tracked. The device then attempts to determine its own location and orientation in the three dimensional space based on the fixed known location of the markers in the space.

In the case of surgical navigation system, it is desirable to have flexibility in tracking items and objects. Moreover, it would be advantageous to avoid having to redesign tools to have fiducial markers "built into" the tool.

In accordance with one aspect of the present application, a fiducial marker is provided with an active independently-powered light emitting device. In this context, the term "independently-powered" means that the power source for the fiducial marker is specific to that marker and is not the same power source used by other fiducial markers, even attached to the same object. In many embodiments, the "independently-powered" aspect is implemented by way of a battery. The battery may be rechargeable in some cases, and may be coupled to a charge circuit that generated a charging current using input energy through an energy conversion component of the charge circuit. Examples include solar energy, kinetic energy, magnetic field energy, wireless radio frequency (non-solar) energy, or other such sources. In some cases, the power source is a charge storage device other than a battery, such as a capacitor coupled to a charging circuit. The charging circuit may receive a charging signal for charging the capacitor for a time, such as an incident RF signal. Persons ordinarily skilled in electronics will be familiar with a range of other mechanisms and variants for storing energy locally in compact form for driving the light emitting device independently from other fiducial markers.

In accordance with another aspect of the present application, a set of fiducial markers for attachment to an object to-be-tracked relies upon marker diversity to reduce the number of fiducial markers necessary for the navigation system to uniquely locate the object. In many existing systems, four or more fiducial markers are arranged in a unique geometric relationship. The fiducial markers may all appear identical to the navigation system (i.e. the system cannot distinguish between the markers) but based on a known geometric relationship between the markers the navigation system is able to determine the three-dimensional orientation of the markers as a set. In accordance with this aspect of the present application, at least two of the fiducial markers attached to an object are distinguishable to the navigation system. In one example, the markers are active markers having light emitting devices (e.g. infrared light emitting diodes) that emit distinct frequencies. The navigation system, for example using filtering, is able to distinguish between the light emitted by the two different markers. In another example, the fiducial markers have the same light emitting devices but emit light using different pulse patterns. For example, one fiducial marker may pulse at a higher rate than the other.

In yet a further aspect, the fiducial markers may include a signal receiver, such as an RF antenna or a photodetector, for example. Using the signal receiver and control logic the fiducial markers may receive signals or commands from the navigation system. For example, the navigation system may send a sync signal to ensure all the fiducial markers are synchronized and pulsing at a desired time and/or rate. In some implementations, the fiducial markers may be addressable, i.e. the navigation system may be capable of transmitting an instruction addressed to a specific fiducial marker. This may enable two-way communication between the fiducial markers and the navigation system. Two-way communication capability may enable the system to obtain battery state or other status information from the markers, alter the pulse pattern of one or more of the markers, alter the output frequency of one of more of the markers, turn one or more of the markers on or off, or cause other functions or operations. Any of a variety of communications protocols may be used by the navigation system and the fiducial markers.

In another aspect, the fiducial markers are structured to replace existing passive fiducial markers without requiring alteration of the frame-and-post structures to which the passive fiducial markers are mounted. That is, the body of the active fiducial marker is designed to be push-fit onto a mounting post. In some instances, the mounting post, when the fiducial marker is mounted, may be used to activate the fiducial marker through serving as an electrical path in the circuit powering the light emitting device, or through causing closure of a switch within the circuit to connect the light emitting device to a power signal.

In yet another aspect, the frame incorporates a master control and sync unit to communicate and, in some cases, power the individual fiducial markers attached to the frame. The fiducial markers in this example are effectively disposable light emitters. The master control and sync unit may control, through a wired or wireless connection, the timing, frequency and pulse rate of the individual light emitters. The master control and sync unit may be able to identify when a light emitter has failed and needs to be replaced. The master control and sync unit may have a wireless communication link with the navigation system to provide status and other information to the navigation system, and to respond to instructions from the navigation system, such as to have the light emitters pulse at a particular rate or in a particular pattern.

Figure 3:
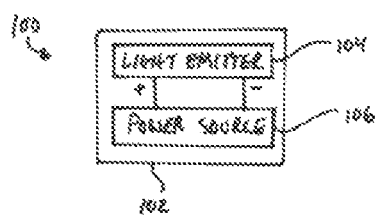
FIG. 3 shows, in block diagram form, a simplified first example of an active fiducial marker.

Reference will now be made to FIG. 3, which shows, in block diagram form, a simplified example of an active fiducial marker 100. The fiducial marker 100 includes a light emitter 104 and a power source 106 housed in a casing 102. The casing 102 includes at least a portion that is at least partly transparent to the output from the light emitter 104. The light emitter 104 may include one or more light emitting diodes (LEDs). The LED may be a visible light LED in some embodiments. In some embodiments, the LED is an infrared LED.

The power source 106 may include a battery. In some cases, the battery may be a "button" cell battery, and may be, for example a lithium, silver oxide, alkaline, or zinc-air or other type of cell battery. Examples of such button cell batteries include those used commonly in hearing aids, key fobs, watches, toys, laser pointers, and the like.

In some cases, the power source 106 is a charge storage device other than a battery. For example, the charge storage device may be a capacitor, and may include a charging circuit that converts another source of energy into a charge current to charge the capacitor, Which is then used to power the light emitter 104. In some cases, the charging circuit may include photodetector or solar cell for charging the capacitor using incident light.

Figure 4:
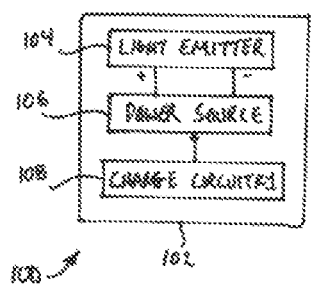
FIG. 4 shows a second example of an active fiducial marker.

As shown in FIG. 4, in one example the fiducial marker 100 includes charge circuitry 108 to charge the power source 106. In some cases, the charge circuitry 108 is for recharging a rechargeable battery. In some cases, the charge circuitry 108 is for temporarily charging a capacitor. The charge circuitry 108 converts an energy source into an electrical current for charging the power source 106. As mentioned above, in some cases the energy source is incident light. In some examples, the energy source may be a magnetic field, an electric field, or kinetic energy.

Figure 5:
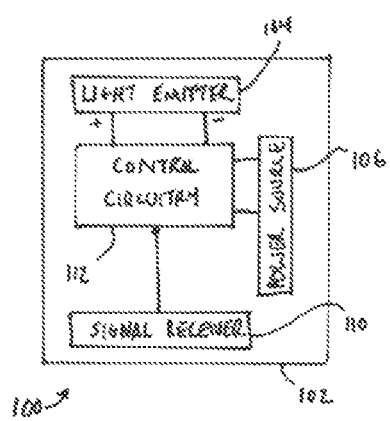
FIG. 5 shows a third example of an active fiducial marker.

Reference is now made to FIG. 5, which shows one example of the fiducial marker 100 that includes a signal receiver 110 and control circuitry 112. The signal receiver 110 may be, for example, a photodetector (photodiode), an RF antenna, a magnetic coil antenna, or the like, for receiving wireless signals from a distant transmitter. The transmitter may be incorporated within the navigation system camera structure, or may be separate from the camera. In one example embodiment, the signal receiver 110 includes a photodiode tuned to receive and detect infrared signals and the transmitter is an infrared LED controlled by the navigation system.

The control circuitry 112 controls a power signal to drive the light emitter 104. In some cases, the control circuitry 112 may generate a constant DC power signal. In some cases, the control circuitry 112 may generate a pulsed on/off power signal having a particular duty cycle and pulse width. In some cases, the pulsed on/off power signal may encode information. For example, information may be encoded using pulse-width modulation, on-off keying, pulse-position modulation, or other forms of modulation. In some embodiments, other signal waveforms (e.g. sinusoidal, etc.) may be used to drive the light emitter 104. In some cases the other signal waveforms may be used together with suitable modulation schemes.

The control circuitry 112 may include a processing device to generate the power signal for the light emitter 104. The control circuitry 112 may include discrete analog circuitry, discrete digital logic elements, integrated circuits, application-specific integrated circuits (ASICs), one or more suitably-programmed general purpose processors or microcontrollers, or combinations thereof. The control circuitry 112 is designed to receive signals induced in and detected by the signal receiver 110. In some cases, the control circuitry 112 may include a demodulator to recover an information signal (e.g. a command) from the detected signal. The control circuitry 112 may implement one or more logic operations that conditionally control the power signal.

In this example, the fiducial marker 100 also includes the signal receiver 110. The signal receiver 110, such as a photodetector, inputs received signals to the control circuitry 112. The control circuitry 112 may demodulate the received signal to obtain information from the transmitter of the received signal, e.g. the navigation system. The demodulated information may include a sync signal, a command, a request, or configuration data, for example. The control circuitry 112 may be configured to generate a power signal in response to the received signal. In some cases, the control circuitry 112 may modulate the power signal with response data in reply to the received signal.

The received information may indicate that the light emitter 104 is to be turned on, turned off, driven with a particular pulse pattern or frequency, etc. In one example, the command may he a request for battery status, in response to which the control circuitry 112 may measure a battery charge level on the battery and encode the charge level in an output power signal to the light emitter 104. In a further example, the control circuitry 112 may be configured to send an acknowledge (ACK) message in response to receipt of a command. In yet another example, the control circuitry 112 may be configured to send an address value in response to a request (in an example in which the individual fiducials are addressable and each stores its unique assigned address value). Other operations or functions may also or alternatively be implemented.

In one example, the control circuitry 112 may be configured to determine the extent to which its own light emitter 104 is occluded by, for example, blood, thereby blocking outbound light. In an example implementation in which the light emitter 104 and the signal receiver 110 emit and sense, respectively, the same RF frequencies, and are co-located in close proximity within the casing 102, it may be possible for the control circuitry 112 to measure the degree of likely occlusion of the transparent portion of the casing 102 through which light is supposed to be emitted and received. It will be appreciated that such techniques would work best with non-visible light (e.g. infrared) so as not to have results skewed by ambient light sources in the operating room.

Figure 6:
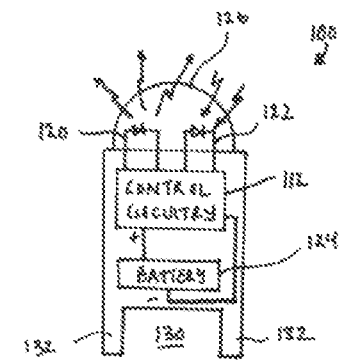
FIG. 6 shows, in block diagram form, a fourth example of an active fiducial marker.

Reference is now made to FIG. 6, which shows, in block diagram form, another example of the fiducial marker 100. In this example, the light emitter is an infrared LED 120 and the signal receiver is an infrared photodiode 122. Both are electrically connected to the control circuitry 112. In this example both the infrared LED 120 and the infrared photodiode 122 are disposed within a domed or curved portion 126 of the casing that is transparent or at least semitransparent to infrared spectrum frequencies. In some cases the transparent portion 126 of the casing is not necessarily curved.

The example fiducial marker 100 further includes a battery 124 as the power source. The battery 124 is electrically coupled to the control circuitry 112. In some embodiments the battery 124 may be replaceable and/or rechargeable. In some other embodiments the casing 102 is sealed and the battery 124 may not be replaceable.

In this example, the casing 102 is structured so as to have a cavity 130 at its lower end. The cavity 130 may be cylindrical in some embodiments, and may be defined by a surrounding downwardly depending wall 132. The cylindrical cavity 130 may be sized so as to allow the fiducial marker 100 to be push fit onto a support post on an object to be tracked.

Figure 7:
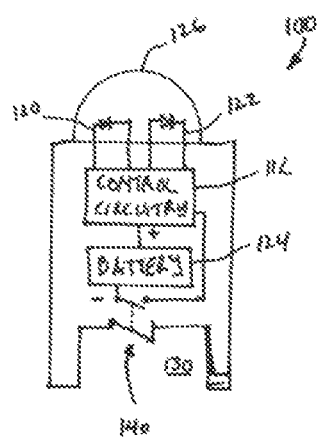
FIG. 7 shows a fifth example of an active fiducial marker.
Figure 8:
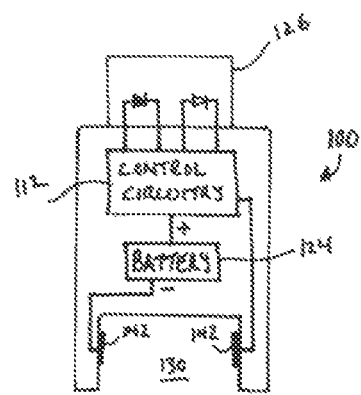
FIG. 8 shows a sixth example of an active fiducial marker.

In some example implementations, two of which are shown in FIGS. 7 and 8, respectively, the coupling between the battery 124 and the control circuitry 112 includes a closure in a normally-open state. In the example shown in FIG. 7 the closure is a switch 140. The casing 102 may be structured to include a mechanical switch that closes the electrical circuit between the battery 124 and the control circuitry 112. The switch 140 may be positioned within the cavity 130, such that it will be closed when the fiducial marker 100 is mounted to a support post. This may help preserve energy when the fiducial marker 100 is not in use.

In another implementation, as shown in FIG. 8, the closure may rely upon the (metal) post itself to close the circuit between the battery 124 and the control circuitry 112. In this example, the cavity 130 features internal contacts 142. When mounted to the metal support post, the post connects the pair of contacts 142 completing the circuit.

Figure 9:
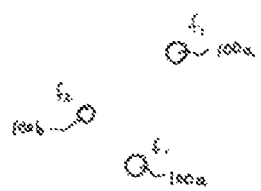
FIG. 9 shows an example geometric arrangement of active fiducial markers using wavelength-based differentiation.

As described above, fiducial markers 100 may emit light at different frequencies. Provided the emissions bandwidths are sufficiently narrow and the center frequencies sufficiently spaced, the light from two fiducial markers 100 may be distinguishable by the navigation system. For example, with infrared LEDs, one fiducial marker 100 may emit light having a wavelength centered at about 850 nm and another fiducial marker 100 may emit light having a wavelength centered at about 940 nm, By emitting light at different wavelengths such that the navigation system is able to identify that a detected fiducial marker 100 is a particular marker in an expected set of markers, the number of such markers required to determine the location and orientation of the set of marker may be reduced and/or the accuracy of the estimates improved. Reference is now made to FIG. 9, which shows a geometric arrangement of fiducial markers 100 (shown individually as 100a, 100b) that a surgical navigation system can locate in a three-dimensional space. The fiducial markers 100 are a set distance from each other. In many cases they are mounted to a frame or other structure attached to the object being tracked. Two of the fiducial markers 100a emit light (infrared in this example) at a first frequency, $f_1$, and the third fiducial marker 100b emits light at a second frequency, $f_2$, different from and distinguishable from the first frequency. The second frequency is "distinguishable from" the first frequency if it is sufficiently spaced from the first frequency, and the bandwidths of the emitted light from the respective markers are sufficiently narrow, that the navigation system is able to independently detect the two types of transmissions.

Because the navigation system is able to differentiate between the marker 100b transmitting the second frequency $f_2$ and the markers 100a transmitting the first frequency $f_1$, the navigation system only requires three markers 100 to locate the geometric arrangement in three-dimensional space. In some implementations, the geometric arrangement includes four or more markers and uses two or more frequencies.

Note that the distance between the marker 100b transmitting the second frequency $f_1$ and one of the markers 100a is different from the distance between the marker 100b transmitting the second frequency $f_2$ and the other of the markers 100a, so as to allow the navigation system to distinguish between the two markers 100a transmitting the first frequency based on their relative proximity to the marker 100b transmitting the second frequency.

Figure 10:
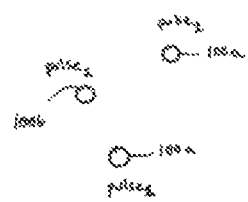
FIG. 10 shows an example geometric arrangement of active fiducial markers using pulse-based differentiation.

In another example implementation, all markers 100 may emit the same general spectrum of light (whether visible, ultraviolet, infrared, etc.), but at least one of the markers 100 pulses their output light at a different frequency than the other markers 100. FIG. 10 shows an example geometric arrangement of markers 100 (shown individually as 100a, 100b). Two of the example markers 100a pulse light with a first pulse pattern and the third marker 100b pulses light with a second pulse pattern different and distinguishable from the first pulse pattern. In one example, the patterns differ in that one is more frequent that the other, although the pulse lengths are the same. In another example, the patterns may feature pulses of different duration. In yet another example, one pattern is "always on", while the other pattern pulses. Other variations will be appreciated having regard to the description herein.

Figure 11:
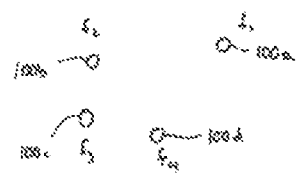
FIG. 11 shows another example geometric arrangement of active fiducial markers using wavelength-based differentiation.

FIG. 11 shows another example geometric arrangement of markers 100 (shown individually as 100a, 100b, 100c, and 100d). In this example, each marker is tuned to emit light at a different frequency such that each marker is distinguishable by the navigation system based on the frequency being emitted. In some examples, the geometric arrangement may include fewer than four or more than four markers.

The use of different wavelength light to distinguish between markers or the use of different pulse patterns to distinguish between markers (or both together) can also or alternatively be used by the navigation system to distinguish between two or more objects being tracked in the operation room. When all the markers are the same, the navigation system requires that the geometric arrangements on different tools be sufficiently distinctive that the system can distinguish one geometric arrangement from another. In one example implementation, two tool may have the same geometric arrangement, but the markers on the respective geometric arrangement feature distinctive wavelengths/frequencies and/or pulse patterns. This may allow for the re-use of the same physical frame for mounting the markers to a tool, rather than requiring a different frame for each tool being tracked during a procedure.

Figure 12:
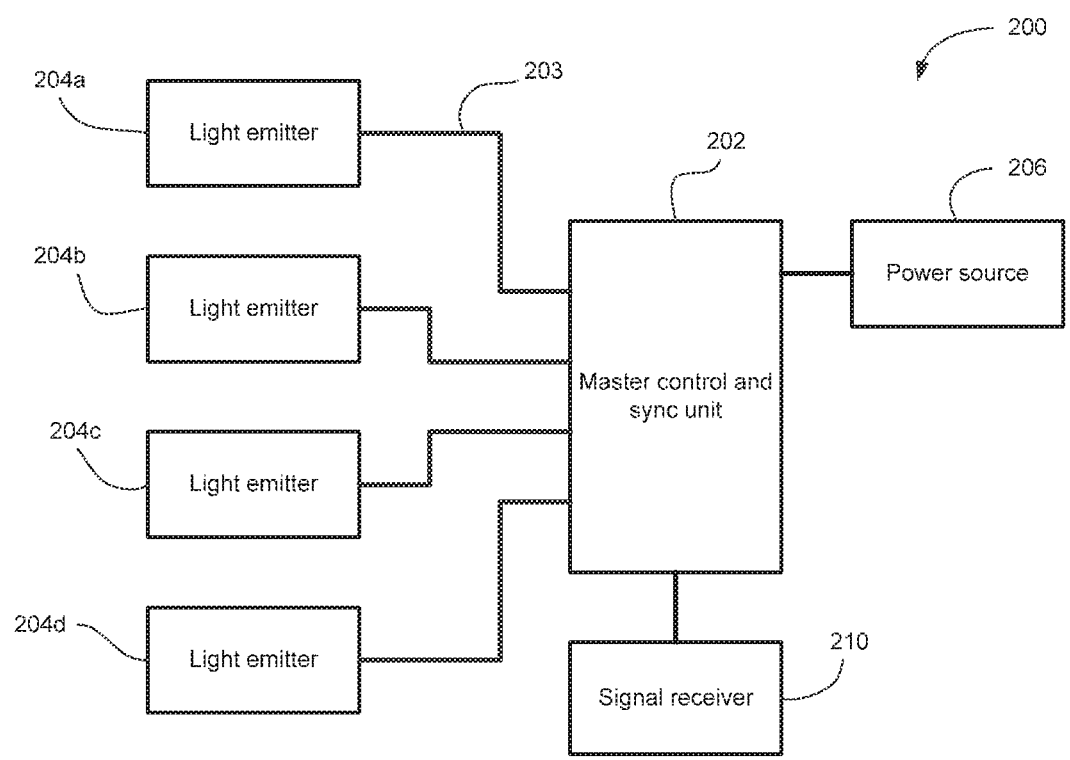
FIG. 12 shows, in block diagram form, an example fiducial marker system for tracking an object in a surgical procedure.

In yet another embodiment, the frame for attachment to the tool and for supporting the individual light emitting diodes includes a control unit coupled to each of the light emitting diodes on the frame. Reference is now made to FIG. 12, which shows a block diagram of one example of a fiducial marker system 200. The fiducial marker system 200 includes a master control and sync unit 202 and a plurality of individual light emitters 204 (shows as 204a, 204b, 204c, 204d). The master control and sync unit 202 is incorporated into the frame used to support the individual light emitters 204. The individual light emitters 204 are mounted to posts or other attachment mechanisms so as to have them positioned in the predetermined geometric arrangement relative to each other. In some embodiments, the frame includes signal lines 203 for the master control and sync unit 202 to supply power and/or commands and other signals to the individual light emitters 204.

The fiducial marker system 200 may further include a power source 206 connected to the master control and sync unit 202, and a signal receiver 210 for receiving and/or sending wireless communication signals. The master control and sync unit 202 may receive instructions or other information from the navigation system via a signal receiver 210. The signal receiver 210 may, in some embodiments, includes transceiver capabilities, thereby enabling the master control and sync unit 202 to send status information and other data to the navigation system using the signal receiver 210. In some cases the signal receiver 210 may include a wireless transceiver, such as a WiFi or Bluetooth™ chip.

The master control and sync unit 202 may coordinate the flashing of the light emitters 204 so as to synchronize their outputs so that they are identifiable to the navigation system camera(s). In some cases, the master control and sync unit 202 may selectively cause one or more of the light emitters 204 to flash at a different frequency and/or pulse rate from the other light emitters 204. In some examples, the master control and sync unit 202 may detect failure of one of the light emitters 204 and may communicate the failure to the navigation system. Failure may be detected through a signal continuity test carried out by the master control and sync unit 202. For example, the master control and sync unit 202 may periodically measure the current and/or voltage across each light emitter 204 and thereby detect an open circuit condition, or other such change, as a failure of the light emitter. In one example, the communication to the navigation system is via the remaining light emitters 204, such as through flashing in a particular pattern, sequence, frequency, etc. The pattern or frequency may indicate which light emitter 204 has failed in some cases.

Figure 13:
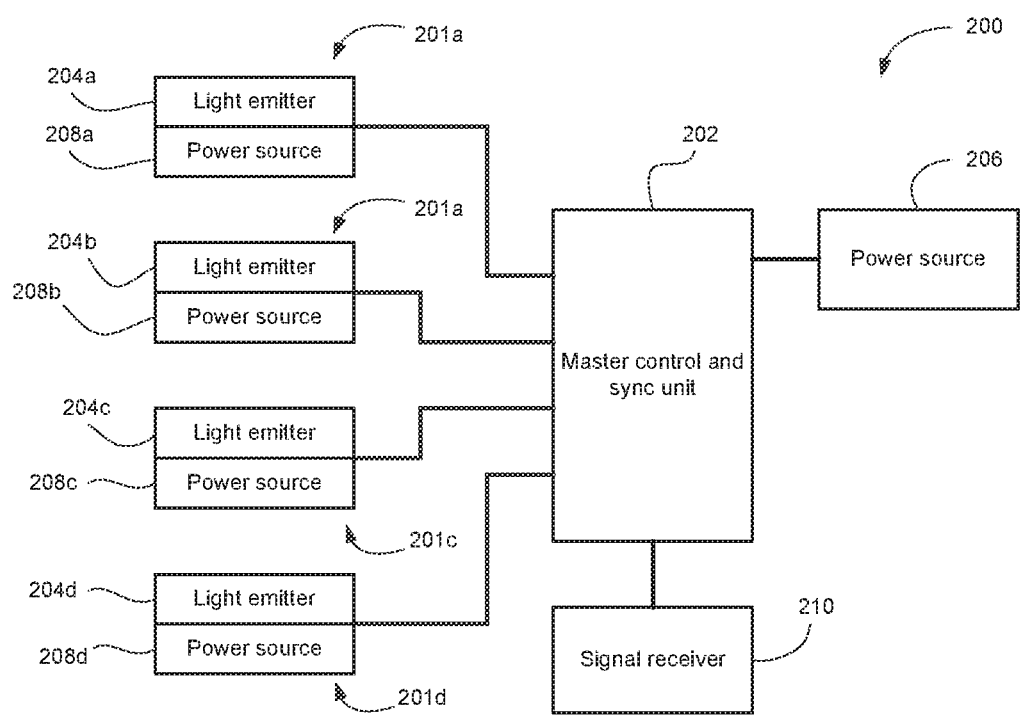
FIG. 13 shows, in block diagram form, another example fiducial marker system for tracking an object in a surgical procedure.

FIG. 13 shows another example embodiment of the fiducial marker system 200. In this example, the system 200 includes individual fiducial markers 201 (shown as 201a, 201b, 201c, 201d) and each fiducial marker 201 includes a respective light emitter 204 and an individual power source 208 (shown as 208a, 208b, 208c, 208d). In this example, the fiducial markers 201 may be similar to those described in connection with FIG. 3 or 4, for instance. In this example implementation, the master control and sync unit 202 does not supply power to the individual fiducial markers 201. In some cases, signals from the master control and sync unit 202 are wired and incorporated in the structure of the frame to which the fiducial markers 201 are mounted. In yet other cases, the signals are wireless and each individual fiducial marker 201 includes a signal receiver to detect and decode signals from the master control and sync unit 202.

The master control and sync unit 202 may be implemented using control logic elements, includes discrete analog components, digital logic components, one or more application-specific integrated chips, one or more microprocessors, one or more microcontrollers, and/or other integrated components. In some cases, the master control and sync unit 202 includes suitable processor-executable instructions stored in memory that, when executed by a processor, cause the processor to carry out one or more of the functions or operations described herein.

Certain adaptations and modifications of the described embodiments can be made. Therefore, the above discussed embodiments are considered to be illustrative and not restrictive.

What is claimed is:

1. A system for active tracking of objects for use in a medical procedure, the system comprising:
    a fiducial frame to be attached to a trackable object, the fiducial frame having a plurality of support posts positioned in a geometric pattern;
    a power source attached to the fiducial frame;
    a master control and sync unit attached to the fiducial frame and coupled to the power source;
    a plurality of fiducial markers, each fiducial marker including a light emitter and a casing for attachment to a respective one of the support posts, the casing defining a cavity that is shaped for mounting to a respective one of the support posts and including a mechanical switch positioned within the cavity for connecting the fiducial marker to the power source, wherein mounting the fiducial marker to a respective support post causes closure of the mechanical switch; and
    signal lines, each signal line connecting one of the fiducial markers to the master control and sync unit.

2. The system claimed in claim 1, wherein each of the fiducial markers further comprises:
    a signal receiver to receive a signal from a surgical navigation system; and
    control logic to control the light emitter in response to the signal from the surgical navigation system.

3. The system claimed in claim 1, wherein the cavity is sized to allow the fiducial marker to be push fit onto said respective one of the support posts.

4. The system claimed in claim 2, wherein the signal receiver comprises a photodetector.

5. The system claimed in claim 2, wherein the control logic comprises a processing device and a memory storing program instructions that, when executed by the processing device, are to cause the processing device to generate a power signal to drive the light emitting component.

6. The system claimed in claim 5, wherein the instructions are to cause the processing device to pulse the power signal at a pulse pattern selected based on the signal from the surgical navigation system.

7. The system claimed in claim 5, wherein the instructions are to cause the processing device to modulate the power signal with response data in reply to the signal from the surgical navigation system.

8. The system claimed in claim 5, wherein the instructions are to cause the processing device to measure a battery charge level of the power source and to modulate the power signal to signal the battery charge level to the surgical navigation system.

9. The system claimed in claim 7, wherein the processing device comprises at least one of a microprocessor, an application specific integrated circuit, or a microcontroller.

10. The system claimed in claim 1, wherein the light emitter comprises an infrared light emitting diode.

11. The system claimed in claim 1, wherein the power source comprises a battery.

12. The system claimed in claim 1, wherein:
    the plurality of fiducial markers include a first active fiducial marker having a first light emitting component that emits light having a first spectral bandwidth, and a second active fiducial marker having a second light emitting component that emits light having a second spectral bandwidth different from the first spectral bandwidth, and
    the system further comprising at least one optical tracking camera to detect and distinguish between light from the first active fiducial marker and light from the second active fiducial marker based upon a difference in the first and second spectral bandwidths.

13. The system claimed in claim 12, the light emitting components comprise light emitting diodes.

14. The system claimed in claim 12, wherein the optical tracking camera further includes a wireless communication source, and wherein each active fiducial marker further includes:
    a signal receiver to receive a signal from the wireless communication source; and
    control logic to control the light emitting component in response to the signal from the optical navigation system.

15. The system claimed in claim 14, wherein the signal receiver comprises a photodetector and the wireless communication source comprises an infrared light.

16. The system claimed in claim 14, wherein the control logic comprises a processing device and a memory storing program instructions that, when executed by the processing device, are to cause the processing device to generate a power signal to drive the light emitting component.

17. The system claimed in claim 16, wherein the instructions are to cause the processing device to pulse the power signal at a pulse pattern selected based on the signal from the wireless communication source.

18. The system claimed in claim 16, wherein the instructions are to cause the processing device to modulate the power signal with response data in reply to the signal from the wireless communication source.

19. The system claimed in claim 16, wherein the instructions are to cause the processing device to measure a battery charge level of the power source and to modulate the power signal to signal the battery charge level to the optical tracking camera.

20. The system claimed in claim 12, wherein the plurality of fiducial markers further includes a third active fiducial marker attached to the fiducial frame and having a third light emitting component that emits light having the first spectral bandwidth, and wherein a first distance between the first light emitting component and the second light emitting component is different from a second distance between the third light emitting component and the second light emitting component.

21. The system claimed in claim 12, wherein the fiducial frame is to be attached to a first tool during the medical procedure, and further comprising a second fiducial frame to be attached to a second tool during an operation, the second fiducial frame having attached thereto a second plurality of independent active fiducial markers each having light emitting components that emit light having a third spectral bandwidth different from the first or second spectral bandwidth.

* * * * *